United States Patent [19]

Scott et al.

[11] Patent Number: 4,763,537

[45] Date of Patent: Aug. 16, 1988

[54] PROCESS FOR PROTECTING ELECTROCHEMICAL SENSORS FROM BIOFOULING IN AN AQUATIC ENVIRONMENT

[75] Inventors: Jonathan R. Scott, College Station; Fredric A. Godshall, Bryan, both of Tex.

[73] Assignee: The Texas A&M University System, College Station, Tex.

[21] Appl. No.: 941,774

[22] Filed: Dec. 15, 1986

[51] Int. Cl.⁴ ............................................. G01N 33/18
[52] U.S. Cl. ..................................... 73/170 A; 354/64
[58] Field of Search ........................ 73/170 A; 354/64

[56] References Cited

U.S. PATENT DOCUMENTS

| | | | |
|---|---|---|---|
| 2,314,372 | 3/1943 | Spilhaus. | |
| 3,748,899 | 7/1973 | Gregg et al. | 73/170 A |
| 3,759,605 | 9/1973 | Johnson | 354/64 X |
| 3,821,894 | 7/1974 | Roeben et al. | 73/170 A X |
| 3,867,630 | 2/1975 | Urban | 73/170 A X |
| 3,969,925 | 7/1976 | Niskin | 73/61 R |
| 4,089,209 | 5/1978 | Grana et al. | 73/61 R |
| 4,092,858 | 6/1978 | Edgerton | 73/170 A |

FOREIGN PATENT DOCUMENTS 2460478 2/1981 France ............................. 73/170 A Primary Examiner—Tom Noland
Attorney, Agent, or Firm—Arnold, White & Durkee

[57] ABSTRACT

A process is described for protecting electrochemical sensors and the like from biofouling—the microbial colonization of sensor surfaces—in an aquatic environment. The process comprises an antibiofoulant gas atmosphere for the sensors between measurement operations. An apparatus is described which allows the practice of the process in a long-deployment, underwater monitoring system.

9 Claims, 5 Drawing Sheets

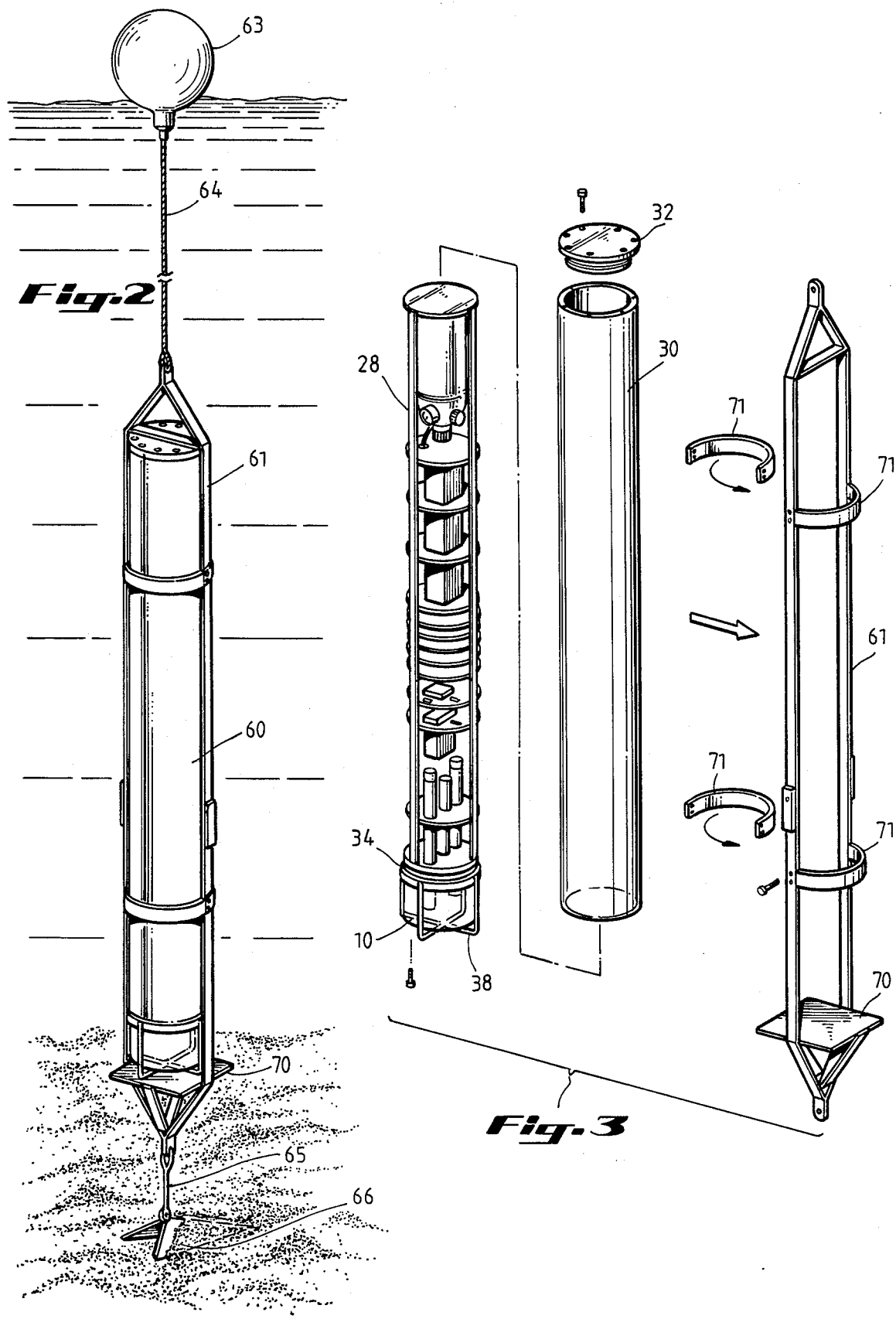

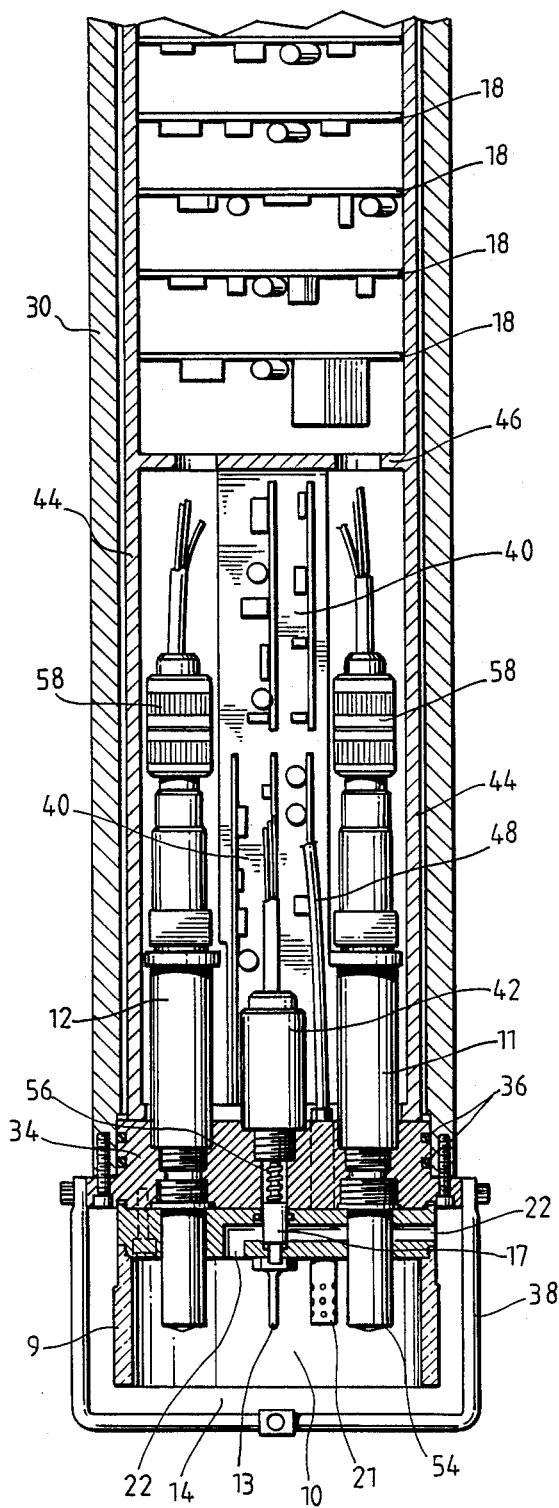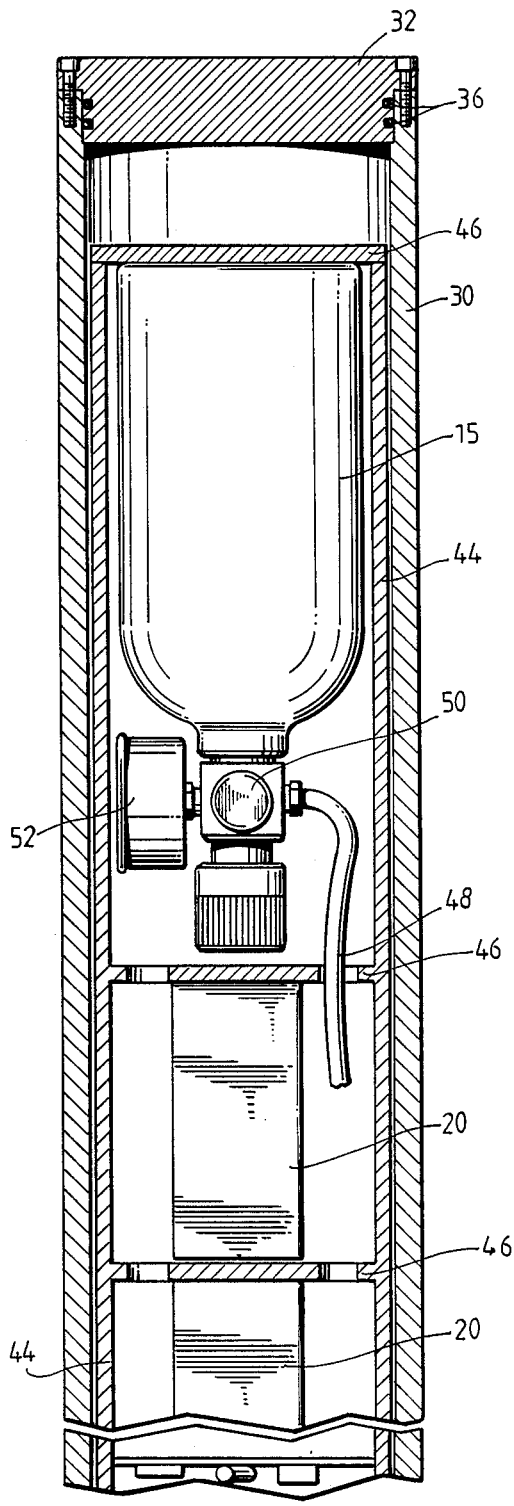

PROCESS FOR PROTECTING ELECTROCHEMICAL SENSORS FROM BIOFOULING IN AN AQUATIC ENVIRONMENT

BACKGROUND OF THE INVENTION

1. Field of the Invention

This invention relates generally to water monitoring systems used in remote, unattended locations employing detectors whose operation is adversely affected by biofouling. Most commonly, the detectors are electrochemical sensors such as dissolved oxygen sensors. More particularly, the invention involves a protection system wherein electrochemical sensors, small electrodes (e.g., coated wires), chemical microsensors, optical probes, and the like in a submersed water monitoring device are exposed to a gaseous antibiofoulant in the intervals between sequential measurement operations. The anti-fouling gas atmosphere inhibits microbial colonization on the sensor surfaces thereby increasing the useful life of the sensors.

Chemical microsensors are broadly defined as small, chemically sensitive systems whose components can be microfabricated. An example of such a system is a micro gas chromatograph which employs a spiral capillary column lithographically defined on a glass microscope slide.

2. Description of the Related Art

In the past, biological fouling organisms in natural waters have prevented the measurement of dissolved oxygen (DO) where frequent tending and cleaning of the sensors is prevented by the remoteness of the measurement location.

The primary limitation of long-deployment dissolved oxygen measurement systems is the tendency of their exposed DO sensors to accumulate biotic fouling. The growth of microorganisms or even macroorganisms commonly degrades the performance of electrochemical dissolved oxygen sensors to the extent that they cannot provide reliable signals.

Dissolved oxygen concentration is a variable of natural water environments which is directly related to the establishment of aerobic/anerobic chemical processes and life processes of all animal life. The productivity of fisheries, for example, has been found to be a function of the dissolved oxygen concentration of the water. Localized conditions of hypoxia (dissolved oxygen concentrations less than 2 milligrams per liter) or anoxia (DO below 100 micrograms per liter) have been implicated in mortalities and migration of commercially important species in bottom waters of the northern continental shelf near Louisiana and Texas. Anoxic conditions along the New Jersey coast during the summer of 1976 resulted in a $60-million loss to the shellfish industry.

Knowledge of the dynamics of dissolved oxygen in natural waters is critical for effective management of water and water-borne resources. At present, an adequate base of time-correlated data on dissolved oxygen, temperature, and salinity is neither available nor obtainable with existing technology. A long-deployment instrument system containing oxygen probes together with temperature and salinity sensors would provide the necessary data for researchers seeking to understand and forecast hypoxic and anoxic events. Without such data, an effective management program for this economically important resource cannot be developed.

In natural waters, conditions of reduced dissolved oxygen are usually established over periods of days, and the concentration will vary irregularly. Monitoring of dissolved oxygen concentration provides the most significant information for analysis purposes when monitoring is performed over time periods which are similar in length to the periods of dissolved oxygen variation. Such time periods can be lengthy, ranging up to a month or more. Because of biofouling, unattended dissolved oxygen and other electrochemical sensors deployed in natural waters usually become fouled with microorganisms before a suitable number of observations can be collected. Thus, what is needed is a data logging system capable of unattended operation without degradation of performance due to biofouling of its sensor elements.

Methods available in the past to prevent fouling of sensor devices have employed the use of toxic materials adhered as a coating on the surface of the sensor. The anti-fouling coating has afforded some protection for a limited period of time, but has also caused a reduction in the sensitivity of the sensor and its general utility. [Edgerton, U.S. Pat. No. 4,092,858 (1978), col. 1, lines 28–34] The present invention, by applying a gas phase antibiofoulant in the time intervals between the measurement phases of operation, avoids the problems associated with toxic antifouling coatings—deterioration over time and reduced sensitivity of the sensor.

Some sewage treatment plants are reported to employ automatic devices which clean dissolved oxygen sensors by periodically withdrawing them from the treatment tanks and directing jets of detergent solution onto their surfaces. Such a treatment system is in part mechanical and in part chemical, but it is clearly impractical for a submersed, remote monitoring system.

Measurement of dissolved oxygen in remote ponds has been done over extended periods by systems utilizing solar powered mechanical lifting devices. The dissolved oxygen sensors are periodically lifted out of the water so as to kill biofoulants by desiccation. This procedure, however, is impractical for monitoring systems which remain submerged.

At least two United States patents address the problem of biofouling on water monitoring devices. Grana et al., U.S. Pat. No. 4,089,209 (1978), "Remote Water Monitoring System," describes an apparatus which collects samples, performs sample analyses with electrochemical sensors, and electronically transmits data to, and receives command signals from a remote station. The solenoid-actuated valves which admit the water samples are said to "operate to eliminate cavities where water could collect and stagnate, and when [opened], operate to remove marine growth attached to the surface of the sampling unit from the path of inflowing water." [col. 2, lines 47–50] The control module of the device is able to store data for subsequent transmission via telemetry upon receipt of an interrogation signal. [col. 3, lines 17–24] The patent addresses the problem of marine organism growth on the surface of the sample unit [col. 5, lines 27–32], but makes no provision for cleaning its electrochemical sensors. Since the sensors remain dry until a water sample is admitted and since sensor readings are taken shortly after sampling, biofouling of the sensors is not likely a problem.

Edgerton, U.S. Pat. No. 4,092,858 (1978), "Oceanographic Sensor with In-Situ Cleaning and Bio-Fouling Prevention System," describes a piezoelectric crystal with sensing elements deposited on, or attached to, the inner and outer surfaces of the transducer or sensing core. [col. 2, lines 36-42] "When excited electrically, at or near resonance, the sensor core vibrates such that all fouling matter is removed from the surface of the sensor and also such excitation prevents any growth to occur." [col. 1, lines 64-67] Cleaning is performed by using greater energy intensity levels than that required for biofouling prevention. [col. 2, lines 10-12] It is said that this system for cleaning or biofouling prevention can be used with any undersea device that can be driven or vibrated in-situ continuously or intermittently by a piezoelectric transducer to cause acoustic streaming and/or cavitation forces. [col. 4, lines 29-34]

Edgerton is addressed to a problem generally similar to that of the present invention, but it relies on ultrasonic vibration to remove or prevent biofouling on the surface of its sensor elements. The sensing elements must be deposited on or attached to the surfaces of an ultrasonic transducer. Edgerton refers to sensing elements fabricated from platinum or gold, or from detector materials such as piezo-resistance materials or other semiconductor materials. [col. 2, lines 36-41] Edgerton makes no mention of dissolved oxygen sensors; nor does he suggest that dissolved oxygen sensors or reference electrodes (e.g., standard calomel electrodes) could be attached to his transducers and function properly. In any case, the present invention follows an approach very different from that of Edgerton.

SUMMARY OF THE INVENTION

The subject invention comprises a system wherein normally submersed water monitoring sensors such as dissolved oxygen sensors, pH electrodes, conductivity probes, and the like are exposed to a gaseous antibiofoulant between measurement operations. In addition to killing or inhibiting the growth of any organisms which may have adhered to the sensors' surfaces during the measurement phase of the operation, the gaseous atmosphere also functions to displace the water from the sample compartment. Thus, the sensors are immersed in the water sample only for the time necessary for them to equilibrate and provide a stable signal. At all other times they are exposed to an antibiofoulant gas atmosphere although the sensors as a whole remain beneath the water surface. By this method microbial colonization of sensor surfaces is prevented or greatly inhibited thereby greatly extending the operational deployment periods of environmental monitoring systems. In a preferred embodiment, the invention creates a gas environment of known composition which can be used for sensor calibration.

The process of this invention includes at least two techniques which function to prevent or greatly inhibit biofouling: (1) limiting the time of contact with the aquatic environment; and, (2) providing a biocidal or bioinhibiting environment between periods of contact with the aquatic environment. This disclosure also describes an apparatus which allows the practice of this process even in a completely submerged remote monitoring device.

In a preferred embodiment designed for monitoring seawater dissolved oxygen content over periods ranging upwards of a month, the subject system comprises a temperature sensor plus two dissolved oxygen sensors which protrude into a cavity. This cavity (the sample compartment) is a cylinder open on its lower end, mounted on the bottom of a housing which encloses the sensor electronics, data recording and control components, batteries, and compressed gas supply. A timer is incorporated in the control system which provides for the periodic sequencing of the sample compartment's operation. In one phase of operation, an electronically-controlled discharge valve on the sample cavity is opened, the cavity is flooded with seawater, and sensor signals are recorded. In the next phase of operation, the discharge valve is closed, a gas inlet valve is opened, and compressed gas from the system's supply forces the seawater from the cavity, creating a gas environment for the sensors. As this gas contains no oxygen, the dissolved oxygen sensors may be calibrated to zero oxygen concentration. The gas used for this operation may itself be an antibiofoulant or, in the alternative, it may contain an aerosol of a liquid antibiofoulant (e.g., carbon tetrachloride). The antibiofoulant kills or inhibits the growth of microorganisms or other marine species which may have been carried into the sample cavity during the flooded phase of operation. The flooded phase of the sample cavity is recreated by the electronically-timed controls which release the gas bubble from the cavity thereby admitting seawater, and the measurement and data storage operations are repeated. This cycle repeats at preselected intervals until all the desired data is obtained and stored.

In a typical cycle-sequence program wherein a ten-minute sampling period occurs every six hours, the sensors are provided with an antibiofoulant gas atmosphere for 23 hours and 20 minutes out of each day. Thus, the sensors are exposed to the aquatic environment less than 3% of the total deployment time.

For measurement operations requiring greater contact time with the aquatic environment, biocides as opposed to bioinhibitors are to be preferred. The single greatest determinant in choosing an antibiofoulant gas will usually be the actual biotic conditions in the deployment area, particularly the kind and number of the locally predominant biofoulants. Obviously, corrosive gases or gases which adversely effect the particular sensors being used should be avoided. Trial-and-error studies may be necessary to establish which antibiofoulant gas is most effective and the minimum ratio of exposure time to antibiofoulant gas to aquatic environment exposure time which will provide adequate protection from biofouling. Since sensors vary in their sensitivity to biofouling, the particular type of sensor for which biofouling protection is being provided will be a major factor in defining the above ratio.

Virtually any sensor subject to biofouling can be protected from such by the practice of this invention. The most common type of oxygen sensors in use today are those which incorporate a gas permeable membrane such as the Clark-principle electrode. Biotic fouling ("biofouling") of the membrane surface is the principal disadvantage to the use of these sensors in long-deployment monitoring systems. Examples of sensors other than dissolved oxygen sensors which may benefit from the practice of this invention include pH-sensitive electrodes such as glass electrodes, ion-specific electrodes, reference electrodes such as calomel electrodes, conductivity probes, and optical devices such as fiber optic probes ("optrodes") for colorimetric or turbidimetric determinations and remote fiber fluorimetry [see, e.g., S. M. Klainer, "In-situ Optrode Measurement of $CO_2$, $O_2$, and $H_2O$ in Plant Systems" Department of Energy, Abstracts of Phase I Awards, DOE/ER-0181/2, 1983]. This invention may also be employed to prevent the biofouling of underwater camera lenses and the like by fitting them with a shuttered extension which can be purged with gas when the shutter opening is closed, thereby providing an antibiofoulant gas environment for the exposed surface of the lens between exposures.

A number of gases may be employed as antibiofoulants in the practice of this invention. The antibiofoulant gases may be biocides or bioinhibitors, substances which create an environment in which marine growth cannot flourish to the extent necessary for biofouling to obtain. It should be understood that even normally non-toxic gases such as nitrogen and the noble gases may function as an antibiofoulant through simple asphyxiation (depriving organisms of oxygen) or by desiccation. Gases which are considered suitable include ethylene, ammonia, argon, bromotrifluoromethane, difluoroethane, dichlorodifluoromethane (Freon 12), and nitrogen. The antibiofoulant gas may comprise an essentially pure gas—e.g., argon. Alternatively, it may comprise a chemical biocide or bioinhibitor dissolved or dispersed as an aerosol in a carrier gas—e.g., iodine in nitrogen. If the electrochemical sensors being protected by the practice of this invention are dissolved oxygen sensors, it is particularly convenient to have the antibiofoulant be oxygen-free. This allows the sensors to be calibrated to zero following equilibration in the antibiofoulant gas atmosphere.

It should be appreciated that to the extent reducing sensor contact time with the aquatic environment effects a diminution in biofouling of sensor surfaces, virtually any gas can be used in the practice of this invention. Gases which are biocides or bioinhibitors in the biochemical sense (i.e., to some extent are toxic to biofoulants) can, of course, be used to greater advantage.

BRIEF DESCRIPTION OF THE DRAWINGS

FIG. 2 depicts the deployment in a body of water of an apparatus which embodies the subject invention.

FIG. 3 shows how the apparatus of the preferred embodiment is inserted in its watertight housing and how the fully assembled apparatus is mounted in a deployment cage.

FIGS. 4A and 4B, taken together, constitute a longitudinal, partially sectioned view of an actual underwater device used for monitoring the dissolved oxygen content of remote marine waters. Lower and upper portions of the device are shown in FIGS. 4A and 4B, respectively. This apparatus employs the subject invention to prevent the biofouling of its dissolved oxygen and temperature sensors.

DETAILED DESCRIPTION OF THE DRAWINGS

Figure 1:
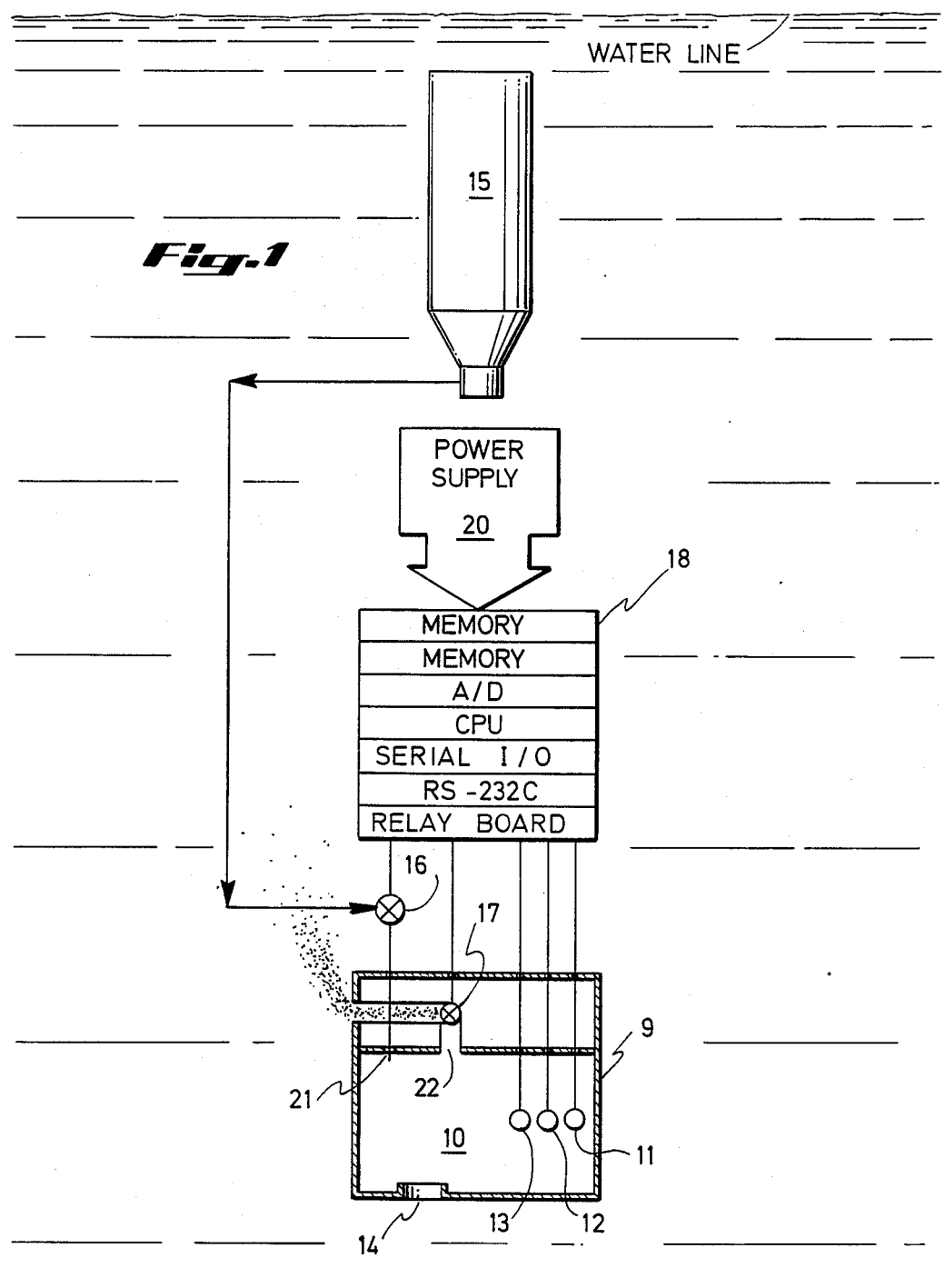
FIG. 1 is a functional drawing of a simple apparatus embodying the subject invention.

FIG. 1 illustrates an apparatus for the automatic, periodic sampling and analysis of natural waters. The apparatus includes a housing 9 defining a cavity 10 into which protrude sensors 11, 12, and 13 whose operation would be adversely affected by biofouling. The sensors may typically be electrochemical sensors, but in a preferred embodiment they include dissolved oxygen sensors such as Clark-principle electrodes. Housing 9 is also equipped with gas inlet 21, gas outlet 22 and water passage 14. Gas inlet 21 and gas outlet 22 are equipped with electrically actuated valves 16 and 17, respectively, which operate under control of the system electronics 18 powered by power supply 20. Gas reservoir 15 is connected to supply a gas at a regulated pressure to valve 16. In actual practice, housing g, gas reservoir 15, electronic controller 18, and power supply 20 are all enclosed in a common assembly or structure adapted to be lowered into a body of water.

The volume of sample cell cavity 10 is preferably the minimum needed to contain the sensors and provide a waterline sufficiently remote from the sensor surfaces to prevent water from contacting them even in the presence of wave action, temperature changes, and/or partial dissolution of the gaseous antibiofoulant in the water. The smaller the volume of the sample cell cavity, the greater the deployment time that can be obtained from the same quantity of antibiofoulant gas.

In operation, the apparatus of FIG. 1 is deployed beneath the surface of a water body, as from a buoy, and is constrained in such a manner that its position in the water column remains substantially unchanged, gas outlet 22 being oriented substantially upwards, toward the surface, and water passage 14 aimed down, away from the surface.

Submersed deployment of a water monitoring device which employs the instant invention is illustrated in FIG. 2. Monitoring system or assembly 60 is mounted within deployment cage 61 which is tethered at its upper end to buoy 63 by line 64. The lower end of deployment cage 61 is attached by anchor line 65 to an anchor 66 embedded in the seafloor. In this manner the monitoring device is constrained in a substantially vertical orientation. The deployment depth may be regulated by adjustment of the lengths of buoy line 64 and anchor line 65. Enough buoyancy can be built into the overall apparatus to keep it buoyant and vertical in the water. Thus, the length of line 65 may be used to keep the apparatus at a particular depth above the bottom; and line 64 may lead to a buoy to act as a marker at the surface.

The assembly of the preferred embodiment in its watertight housing and the mounting of the assembled monitoring system in deployment cage 61 is shown in FIG. 3. Internal chassis 28 supporting the system's internal components shown in FIG. 1 is inserted into tubular member 30 of the housing until the flange of lower bulkhead 34 engages the lower end of the tube. A watertight seal at the upper end of housing tube 30 is provided by bulkhead 32. Lower bulkhead 34 is secured to housing 30 with sample cell 10 extending downward, below the lower limit of watertight housing 30. Cell guard 38 of the assembled monitor rests on platform 70 of deployment cage 61. Clamp segments 71 secure the monitor in deployment cage 61.

A typical operation sequence of the apparatus functionally illustrated in FIG. 1 is as follows. First, system electronics 18 selects gas discharge valve 17 open and gas inlet valve 16 closed. The gas in sample cavity 10 escapes through gas outlet 22, allowing water to enter sample cavity 10 through water passage 14. Following equilibration, sensor readings are automatically logged by system electronics 18. When the data logging operations are completed, system electronics 18 selects gas discharge valve 17 closed and gas inlet valve 16 open. Antibiofoulant gas from reservoir 15 then enters cavity 10 under pressure via gas inlet 21, displacing the water sample contained therein which is forced out of the cavity via water passage 14. After a time interval sufficient to ensure that substantially all the water contained in cavity 10 has been displaced, system electronics 18 selects gas inlet valve 16 closed, and cavity 10 now contains antibiofoulant gas of known composition. Microorganisms or other marine species adhering to the sensors are killed, or their growth is substantially prevented, by contact with the antibiofoulant gas. After a preselected time interval has elapsed, the cycle is repeated. In this manner a series of sensor measurements at known time intervals may be automatically taken and stored until such time as either power supply 20 or the gas supply in reservoir 15 is exhausted. The sensors are exposed to the marine waters only for the time necessary for equilibration and measurement. At all other times they are exposed to an antibiofoulant gas environment. In this way biofouling of the sensors' surfaces is prevented.

The apparatus may optionally be equipped with stirring means to circulate the water sample in the vicinity of the sensor electrodes. Stirring may advantageously be used to prevent the formation of a boundary layer adjacent to electrode sensor surfaces, thus assuring that the readings taken reflect the bulk properties of the sample. A particularly convenient stirring means is a magnetic stir bar within the sample cell driven by a rotating magnet located on the other side of the sample cell top member.

Sensors 11, 12, and 13 are selected to be responsive to the parameters of interest of the water body. Since in most cases the sensors are exposed to zero values of the parameters sensed when cavity 10 is filled with antibiofoulant gas, sensor zero-point calibration can be accomplished in the presence of the gas.

FIGS. 4A and 4B depict a dissolved oxygen measurement system for natural waters which employs the subject invention to alleviate the problem of sensor biofouling. The system is adapted for long-term monitoring of remote ocean sites. Periodic sensor readings are stored internally in semiconductor memory. The stored data is read by connecting an internal microprocessor to a host computer following recovery of the apparatus.

The apparatus of FIGS. 4A and 4B comprises an elongated, cylindrical housing comprising tube 30, closed at its upper and lower ends by bulkheads 32 and 34, respectively. Internal chassis 28 comprising longitudinal frame members 44 and transverse frame members 46, is supported internally of the housing by the attachment of lower bulkhead 34 to housing tube 30. Supported by the chassis are batteries 20, a gas pressure cylinder 15, system control and data logging electronics 18, and sensor electronics 40. Openings with watertight seals are provided in lower bulkhead 34 for mounting sensor electrodes 11-13.

Upper and lower bulkheads 32 and 34 are sealed in a watertight relation to housing tube 30 by means of O-ring seals 36. The sample cell, comprising walls 9 defining sample cavity 10, is mounted to lower bulkhead 34 and extends downward, assuming the configuration of an inverted drinking glass, the open end of which comprises water passage 14. Sensor electrodes comprising dissolved oxygen probes 11 and 12 and temperature probe 13 are mounted in lower bulkhead 34 and protrude into sample cell cavity 10. The electrodes are positioned such that their sensing elements (e.g., 54) are above the waterline in the sample cell cavity 10 when the sample cell is in the gas-environment state. Electrical connectors 58 attach the electrodes to the sensor electronics 40. Sample cell guard 38 protects the sample cell from mechanical damage and supports the apparatus in the deployment cage.

Figure 5:
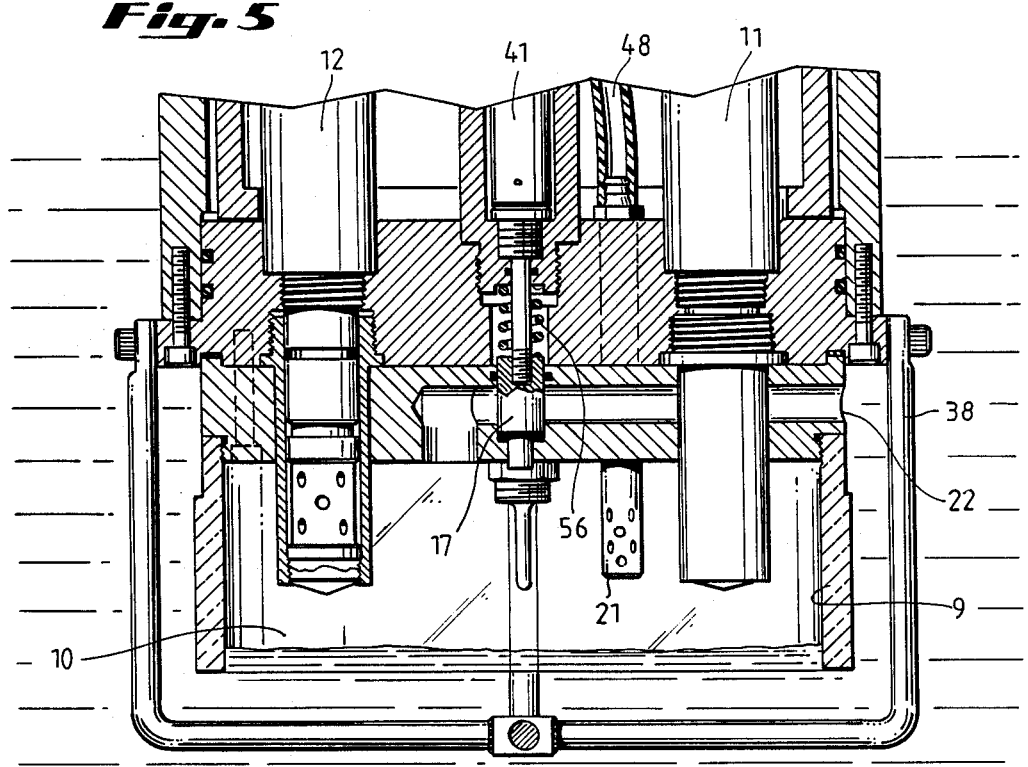
FIG. 5 is a longitudinal, partially sectioned view of the lowermost portion of the preferred embodiment showing the sample cell and adjacent components. The gas discharge valve is shown in its closed condition. One dissolved oxygen sensor is shown in cutaway view, the other in plan view.
Figure 6:
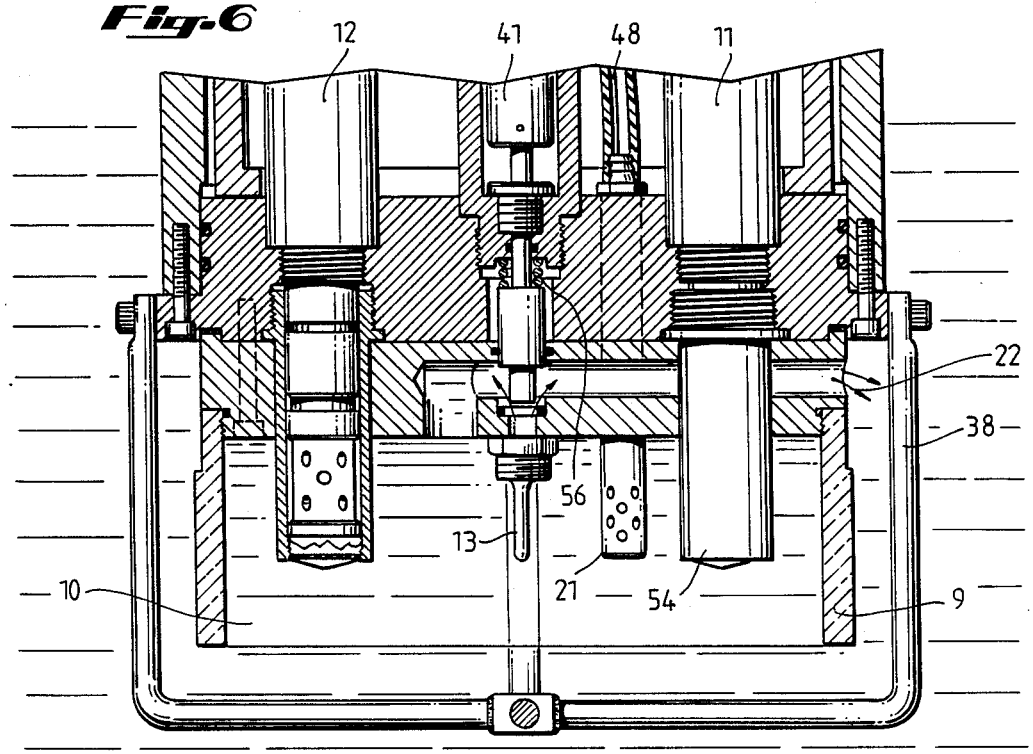
FIG. 6 is a longitudinal, partially sectioned view of the lowermost portion of the preferred embodiment showing the sample cell and adjacent components. The gas discharge valve is shown in its open condition. One dissolved oxygen sensor is shown in cutaway view, the other in plan view.

The upper end of the sample cell is fitted with gas outlet passage 22 which is opened and closed by gas discharge valve 17. An electrical pull-type tube solenoid (42) operates gas discharge valve 17 in response to signals from system control electronics 18. FIGS. 5 and 6, respectively, detail gas discharge valve 17 in its closed and open conditions. Upon actuation, plunger 41 of solenoid 42 retracts, compressing spring 56, and opening gas discharge valve 17. When solenoid 42 is deactuated, spring 56 returns gas discharge valve 17 to its closed position.

Antibiofoulant gas is stored in pressure cylinder 15 which is fitted with pressure gauge 52 and pressure regulator 50. Gas from pressure cylinder 15 is supplied via tubing 48 to gas inlet 21 of the sample cell.

While the system is on the surface, an RS-232-C port connected to the instrument's microprocessor allows communication to a host computer. This allows the user to selectively input the instrument's start day and time, elapsed time between each sample (hours and minutes), duration of sample period (minutes), number of readings during sample period, and purge and flood times. After the sequencing instructions have been input, the system is hermetically sealed in a pressure casing capable of withstanding pressures to a depth of 34 meters. The instrument is then deployed in the water column with the onboard microprocessor controlling the sampling sequence. Following deployment, the instrument is brought to the surface and data dumped to a host computer using the same RS-232-C port. Each data record is identified with the day and time followed by data fields for dissolved oxygen and temperature corresponding to the number of read cycles input previously. The last data field represents the oxygen concentration in the sample cell when water is absent and the antibiofoulant is present. This allows normalization of the data and is also used as a system check.

In operation, system control electronics 18 actuates electrical solenoid 42 which retracts, opening gas discharge valve 17 which allows gas within sample cell cavity 10 to escape via passageway 22. The escaping gas is replaced with seawater which enters via water passageway 14. Following a period of equilibration, readings from dissolved oxygen sensors 11 and 12 and temperature probe 13, amplified and processed by sensor electronics 40, are sampled and stored in the memory circuits of system control and data logging electronics 18. If the apparatus is fitted with sample stirring means, circulation of the water sample within the sample cell during the measurement phase of operation may be accomplished.

Following completion of the measurement operations, solenoid 42 is deactuated, allowing spring 56 to return gas discharge valve 17 to its closed condition. Next, an electrically-actuated gas valve [not shown] is opened in response to a signal from system control electronics 18 and antibiofoulant gas from gas cylinder 15 at a pressure selected by adjustment of regulator 50 flows via gas tubing 48 to sample cell gas inlet 21. The incoming antibiofoulant gas displaces the water sample which exits via water passageway 14. A particularly suitable gas inlet valve is the Minimatic Poppet Valve No. EV-3M-6VDC manufactured by Clippard Instrument Laboratories, Inc. of Cincinnati, Ohio.

After a preselected time interval, the gas flow is stopped by closing the gas inlet valve and the electrodes are allowed to equilibrate in the gas atmosphere existing in sample cell cavity 10. Dissolved oxygen sensors 11 and 12 may now be calibrated to correspond to the known oxygen content of the antibiofoulant gas. This cycle is repeated at preselected time intervals until the desired quantity of data is gathered and stored. Following retrieval at the end of the deployment period, the stored data is read by connection to a host computer.

Typical cycle sequence times for the apparatus illustrated in FIG. 4 are as follows:

(1) The gas discharge valve (17 in FIGS. 4, 5 and 6) is opened for a minimum period of 3 to 4 seconds to flood the sample cell cavity with a water sample.

(2) Following a 5-minute delay for sensor equilibration, sensor readings are sampled and stored.

(3) Following an additional 5-minute delay, duplicate sensor readings are sampled and stored.

(4) The gas inlet valve is then actuated for a period sufficient to ensure that substantially all of the water is displaced from the sample cell cavity. The actual time necessary to accomplish this displacement depends on the gas supply pressure and the depth of deployment. With the gas supply regulator set at 60 psi, a 30-second gas flood time has been found sufficient when the apparatus is deployed at a depth of 40 feet.

(5) A 2-hour delay ensues, then the cycle repeats.

The date and time of the first sample taking can be programmed into the system control electronics prior to deployment, as can the total number of sample readings desired.

Figure 7:
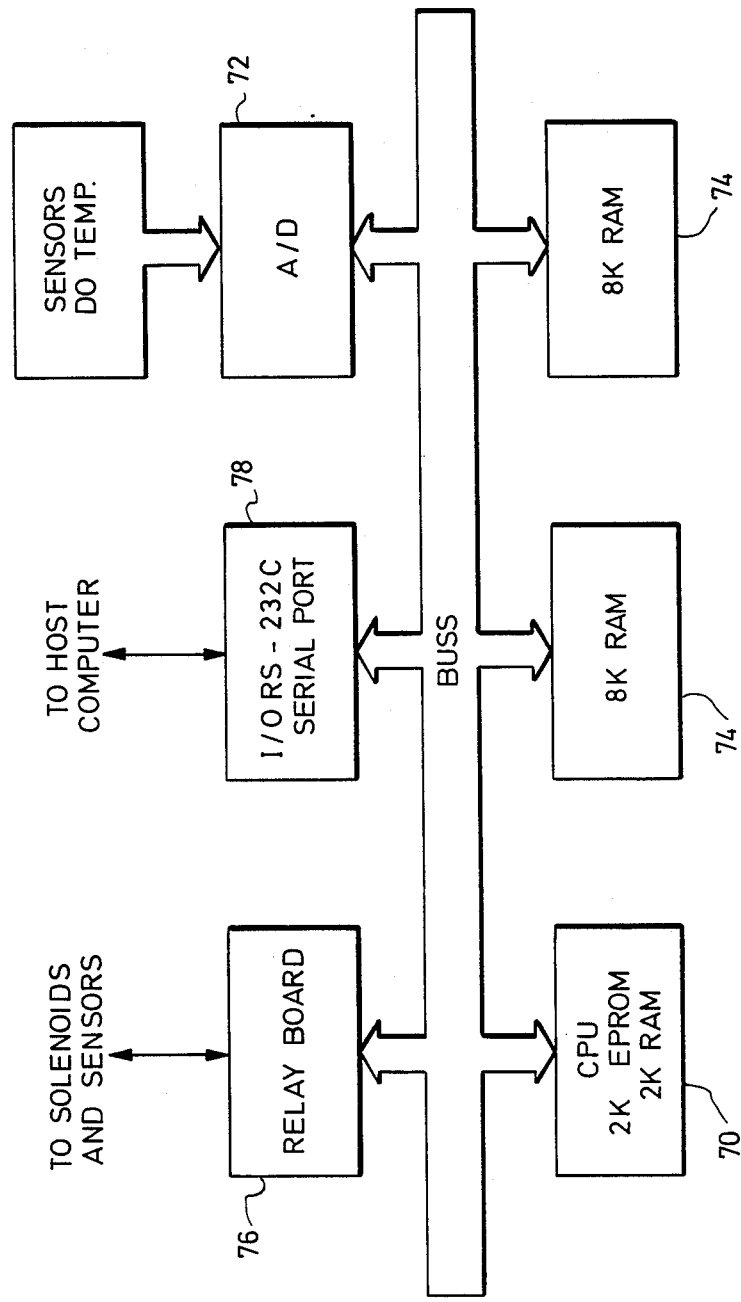
FIG. 7 is a block diagram of the system control and data logging electronics used in the underwater device shown in FIG. 4.

FIG. 7 depicts in block form the control and data logging electronics of the dissolved oxygen measurement system shown in FIG. 3. A microprocessor (70) such as a Zilog Z80 is provided with pre-programmed instructions stored in erasable programmable read-only memory (EPROM). To enable maximum deployment times, the microprocessor will most preferably be of the low power, CMOS type. Associated with the microprocessor is semiconductor random access memory (RAM) 74 for data storage.

A clock circuit with a quartz-crystal oscillator is connected to the microprocessor to provide time signals for data logging and sample sequencing.

An input/output (I/O) circuit (78) with an RS-232-C serial data port provides data communications capability. Analog signals from temperature and dissolved oxygen sensors (T and DO, respectively) are digitized by analog-to-digital converters 72 and read into memory 74. Electric solenoids for actuating the discharge valve and gas supply valve are controlled by relays on relay board 76 which are responsive to signals from microprocessor 70.

Data stored by the system in RAM is read by a host computer following retrieval. Connection is made via the RS-232-C serial data port of the I/O circuit.

It will be recognized that a number of variations may be made in the practice of this invention without departing from the spirit and scope of the invention. Thus, storage batteries, alone, or in combination with solar electrical power generators may be adapted to serve as the power source for the apparatus. A floating solar panel containing photovoltaic cells connected to rechargeable batteries could be tethered to the deployment buoy shown in FIG. 2. To extend the deployment time, an electrical power lead extending from the solar panel to the submersed monitoring device could then be used to supplement or even replace the internal power supply.

What is claimed is:

1. A process for reducing biological fouling of a sensor deployed beneath the surface of a body of water which comprises creating a gas environment substantially free of such water for the sensor between sensing operations while the sensor as a whole remains beneath the water surface and is directly exposed to the water during sensing operations.

2. The process recited in claim 1 wherein the gas is a biocide.

3. The process recited in claim 1 wherein the gas is a bioinhibitor.

4. The process recited in claim 1 wherein the gas is selected from the group composed of ethylene, ammonia, bromotrifluoromethane, difluoroethane, dichlorodifluoromethane, nitrogen, and the noble gases.

5. The process recited in claim 1 wherein the gas is a mixture comprising a biocide dispersed in a carrier gas.

6. A process for sensing a parameter characteristic of a body of water which comprises:

(a) immersing in said body of water a sensor capable of generating an electrical signal representative of the value of said parameter;

(b) detecting an electrical signal generated by said sensor;

(c) displacing said water from around said sensor, while continuing to immerse said sensor in said body of water with a gaseous antibiofulant in a quantity and for a time sufficient to reduce any biological fouling of said sensor; and thereafter displacing said gas from around said sensor with water from said body of water.

7. A process as recited in claim 6 wherein the sensor is a dissolved oxygen sensor.

8. A process for reducing biofouling of optical devices deployed beneath the surface of a body of water which comprises creating a gas environment substantially free of such water for the surface of the optical element exposed to the water during sensing operations by displacing water from such surface with a gas for a time sufficient to inhibit the growth of biofoulants.

9. A process as recited in claim 8 wherein the gas is a biocide.

* * * * *